United States Patent
Groiso (10) Patent No.: US 8,211,109 B2
(45) Date of Patent: Jul. 3, 2012

(54) OSTEOSYNTHESIS CLIP AND INSERTION TOOL FOR INSERTING AN OSTEOSYNTHESIS CLIP INTO BONE TISSUE FRAGMENTS

(75) Inventor: Jorge A Groiso, Buenos Aires (AR)

(73) Assignee: Medicrea International, Neyron (FR)

( * ) Notice: Subject to any disclaimer, the term of this patent is extended or adjusted under 35 U.S.C. 154(b) by 1693 days.

(21) Appl. No.: 11/197,174

(22) Filed: Aug. 4, 2005

(65) Prior Publication Data

US 2005/0273108 A1    Dec. 8, 2005

Related U.S. Application Data

(63) Continuation of application No. 10/634,410, filed on Aug. 5, 2003, now Pat. No. 7,635,367.

(51) Int. Cl.
*A61B 17/064*    (2006.01)

(52) U.S. Cl. .......................................... 606/75

(58) Field of Classification Search .................... 606/72, 606/75, 115, 151, 154–157, 215, 217, 219–221
See application file for complete search history.

(56) References Cited

U.S. PATENT DOCUMENTS

| | | | |
|---|---|---|---|
| 5,246,443 A * | 9/1993 | Mai | 606/78 |
| 5,449,359 A | 9/1995 | Groiso | |
| 5,660,188 A | 8/1997 | Groiso | |
| 5,827,283 A | 10/1998 | Groiso et al. | |
| 5,853,414 A | 12/1998 | Groiso | |
| 5,947,999 A | 9/1999 | Groiso | |
| 5,993,476 A | 11/1999 | Groiso | |
| 6,966,911 B2 | 11/2005 | Groiso | |
| 7,618,441 B2 | 11/2009 | Groiso | |
| 7,635,367 B2 | 12/2009 | Groiso | |
| 2003/0167072 A1 * | 9/2003 | Oberlander | 606/232 |
| 2005/0021035 A1 | 1/2005 | Groiso | |
| 2010/0082030 A1 | 4/2010 | Groiso | |
| 2010/0087822 A1 | 4/2010 | Groiso | |

* cited by examiner

*Primary Examiner* — Thomas C. Barrett
*Assistant Examiner* — Michael Araj
(74) *Attorney, Agent, or Firm* — Ostrolenk Faber LLP

(57) ABSTRACT

An improved osteosynthesis clip for the cicatrization of bone fragments, an improved insertion tool and method for inserting the improved clip and a surgical system implementing the improved clip and insertion tool are provided. The clip includes at least two engagement legs extending approximately parallel to one another and including insertion tips to be inserted into the bone tissue fragments; and a connecting bridge coupled to the at least two engagement legs at portions opposite the insertion portions, the connecting bridge including at least two elongated sections extending along side one another, the elongated sections extending along a non-linear trajectory to form a non-linear deformable region, such as a depression or a dome, wherein the engagement legs having respective helical screw surfaces extending substantially an entire distance between respective insertion and opposite portions to facilitate removal of the clip after the bone tissue fragments have fused. The improved clip may be made of any biocompatible material, including shape memory alloys, such as Nitinol. The insertion tool is improved to apply force at the bridging tips of either a stepped on a non stepped clip.

26 Claims, 11 Drawing Sheets

OSTEOSYNTHESIS CLIP AND INSERTION TOOL FOR INSERTING AN OSTEOSYNTHESIS CLIP INTO BONE TISSUE FRAGMENTS

RELATED APPLICATION DATA

The present application is a continuing application, claiming the benefit of co-pending parent application Ser. No. 10/634,410 filed on Aug. 5, 2003, published Mar. 3, 2005 and entitled "OSTEOSYNTHESIS CLIP AND INSERTION TOOL FOR INSERTING AN OSTEOSYNTHESIS CLIP INTO BONE TISSUE FRAGMENTS", Publication No. 2005/0049600 (hereinafter the "'600 App.") the entire contents of which are expressly incorporated herein by reference.

FIELD OF THE INVENTION

The present invention relates to an improved osteosynthesis clip having improved structural properties and an improved apparatus and method for inserting and removing the osteosynthesis clip into and from bone tissue fragments, and having an improved insertion tool for inserting the osteosynthesis clip into bone tissue fragments.

BACKGROUND INFORMATION

There are various known elements (e.g., casts and internal elements, such as screws, plates, clips, etc.) and methods for permitting the cicatrization of bone parts and/or fragments by holding them together and avoiding their relative movement to the greatest degree possible. For example, an osteosynthesis clip as described in the above mentioned co-pending parent application (hereinafter the "'600 App."), in addition to clips as described in U.S. Pat. Nos. 5,449,359, 5,660,188, 5,947,999, 5,853,414, and 5,993,476, the entire contents of which are expressly incorporated by reference, refer to elastic clips and methods for osteosynthesis that connect at least two bio-organic tissue members and for aiding osteosynthesis between bone fragments when it is necessary to maintain contact between the severed parts for the duration of the process of re-joinder between them. As described in the '600 App., the clip includes at least two engagement legs extending approximately parallel to one another and including respective distal bridging tips (hereinafter "bridging tips" or "bridging portions") and respective proximal insertion tips (hereinafter "insertion tips" or "insertion portions") to be inserted into the bone tissue fragments; and a connecting bridge coupled to the bridging tips of the two engagement legs, the connecting bridge including at least two elongated sections extending along a non-linear trajectory to form a non-linear deformable region, such as a depression or a dome.

As further characterized in the '600 App., bone fragments to be joined are first drilled in locations for later receiving respective engagement legs of the elastic clip. ('600 App., ¶2). Additionally, the clips are capable of receiving soft tissue members, such as muscle, tendons or ligaments, to be joined to the bone members during the osteosynthesis process. (U.S. Pat. No. 5,947,999, FIG. 24-26 (the "'999 patent")). If necessary, the soft tissue members can be held in place by the clips while also holding bone fragments in place by sliding the soft tissue members between the bridge and bone portions. ('999 patent, col. 7, 1.60 to col. 8, 1.8). Once the insertion tips of the legs are inserted into the bores drilled in the bone fragments to be joined, the elastic clip is grasped by an instrument, and, using a suitable percussion tool, the instrument is struck to push the clip into the bone fragments. ('600 App., ¶2). Once the legs are completely inserted into their respective bores, the elongated bridge sections of the clip are separated by the tool, which causes the legs to approach one another, thereby carrying the bone fragments into frictional contact under pressure. ('600 App., ¶2).

It has been found that, if the elongated bridge sections of the clip are over-separated, for example, by a surgeon applying too much separation force on the elongated bridge sections, then the contact pressure between the bone fragments in an area near the bridge of the clip may exceed the contact pressure between bone fragments in an area near the bone fragments furthest from the bridge. This pressure differential may cause the bone tissue fragments to pivot toward the bridge of the clip, thereby causing a deviation of the longitudinal axis of the bone fragments and the formation of a gap between the fragments, especially nearest the insertion tips of the engagement legs.

A known solution to this shortcoming is a clip having a non-linear deformable region, such as a depression, provided along the elongated sections of the clip. ('600 App., FIGS. 1, 2, 3a-3d). After the clip is inserted into drilled holes in each bone fragment on either side of the fracture, a first force is applied on the elongated bridge sections to separate the opposed elongated sections of the bridge section. This causes the engagement legs to move toward each another. However, the legs may pivot in such a way that a gap may be formed at the portion of the fracture opposite the clip. ('600 App., FIG. 3c). A second force, such as an upward force, is applied in the non-linear deformable region of the bridge sections thereby causing a partial linearization of the non-linear deformable region. This second force causes the inserting portions to pivot toward one another about the bridging portions, thereby causing any gap to close between the bottom surfaces of bone tissue fragments. ('600 App., FIG. 3d). While applying the second force to the elongated sections, withdrawal of the clip from the bone fragments may be prevented by simultaneously applying a third force opposite to the second force, such as a downward force, on the bridge section near the bridging portions of the engagement legs. However, in the case of a stepped clip, as illustrated in FIGS. 4a and 4b of the '600 App., for joining bones of different diameter, it has been found that the known insertion tool, as claimed in the '600 App., and the patents referenced therein, requires improvement for better engaging the bridging tips of the engagement legs in order to apply the third force. Also, the tool must be configurable to be reusable on either a non-stepped or a stepped clip. As will be shown herein, the tool is incapable of engaging the stepped clip in a stepped down region in order to apply the third force at that region and thereby can not effectively counter the second force applied to the non-linear deformable region. The present invention addresses this issue.

It has further been found that the known removal procedures of a clip from the bone fragments can cause excessive damage to the bone fragments. One manner in which the bone fragments are damaged is by the traction forces created when clips having spikes or retaining teeth for gripping the bone are removed from bone fragments with a direct sheer force formed by pulling the clip transversely from the bone with forceps. Also, such a direct linear removal of the clip often requires insertion of a lever between the clip's bridge and the bone surface to pry the clip from the bone. The traction forces associated with such removal procedures causes the retaining teeth to tear the original bony channel as they exit the bone, causing trauma. Moreover, such traction forces can further damage the bone by causing splints or fractures and can further thwart the intended healing process by causing undesired displacement of the bone fragments. To the extent that clips have employed screw-like threads to advantageously facilitate the removal of the clip after the bone tissue has been fused (See '600 App., FIG. 8a-8c), this also has shortcoming to which this invention is directed. Removal is obtained by cutting away the bridge at the locations of bridging tips 140a and 140b to remove the bridge, as shown in FIG. 8b of the '600 App. Once the bridge is removed, the engagement legs may be removed from the bone tissue, for example, by separately unscrewing each engagement legs in a counterclockwise direction, as shown in FIG. 8c of the '600 App. However, the known clips, as presented in the '600 App., have only partially threaded legs—either provided near the insertion tips or, alternatively, near the bridging tips. Therefore, upon removal, the threaded region cuts through the boney channel of the area of the bone corresponding to areas of the engagement members that were not threaded. (See '600 App., FIGS. 8a-8c). The present invention addresses this issue by redesigning the engagement legs with more effective threading.

Additionally, with the advancement of thorascopic surgical techniques requiring the insertion of tools through small tubes and openings to perform ever more delicate surgeries, i.e. spinal surgery, it is also advantageous to limit the number of tools that are used and the amount of manipulation required to position the clip. Therefore, the use of thermally sensitive materials or shape memory alloys for creating the necessary deformation of the bridge member as opposed to physical manipulation by tools is advantageous. As such, the present invention solves these problems associated with the known tools and the required physical manipulation of the clip by incorporating shape memory alloys into the improved clip. In and of themselves, shape memory alloys such as Nitinol have been well known. See for example, U.S. Pat. No. 3,174,851. Other metals, such as AuCd, FePt.sub.3, beta Brass and InTI, also exhibit shape memory behavior. These materials have the property of changing shape in response to a change in material temperature. This shape change potential is imparted into the memory metal device through a series of heat treatments. The transition temperature range is imparted to the material through varying mixtures of intermetallic compounds such as nickel-titanium and heat treatment. The heat treatment methods for the material generally consist of at a minimum high temperature setting of the desired final shape of a device followed by a low temperature straining of the device to a second shape. Then, when the device is in the second shape and brought to the transition temperature the device returns to the preprogrammed final shape. The shape change occurs due to the transition of the material from a martensitic to austenitic phase microstructure. These heat-initiated changes cause gross changes in the shape of the implant formed from memory metal. Further detail regarding the creation and properties of shape memory alloys can be found in U.S. Patent Application Publications 2002/0029044 to Monassevitch, 2004/0172107 to Fox and 2002/0173793 to Allen, all of which are fully incorporated by reference.

SUMMARY OF THE INVENTION

It is an object of the present invention to avoid the disadvantages of known osteosynthesis clips described above. For this purpose, the present invention provides at least one surface of the engagement legs of the known clips with a threaded gripping surface substantially along an entire distance between the insertion tips and the bridging tips opposite the insertion tips. The gripping surface of the improved clip is screw-like, having an inclined thread. The thread may include a cutting edge for easily cutting through bone. Therefore, when the improved clip is inserted into the bone fragments, the threaded gripping surface extends the entire length of the engagement leg in the bone fragments. Depending on the arrangement of the thread, the amount of cutting into the bone required when removing the engagement legs therefrom would at most cut a new path in the bone for one complete turn of the leg members as opposed to past designs which required bone cutting to occur throughout the entire removal process. For example: if the engagement legs have threading completely surrounding a circumference of the engagement legs then there will be minimal cutting or possibly even no cutting of a new path when removing the legs from their bores. Also, if, for example, only one side or one edge of the legs are threaded then, at most, a new path will be cut in the bone for the duration of one complete turn of the legs upon removal.

It is another object of the present invention to provide an improved osteosynthesis clip that is manufactured, at least partially, form shape memory alloys. Shape memory alloys remain subject to physical manipulation but have the added benefit of heat induced deformation. Therefore, a clip made from shape memory alloys may be brought to its desired final position either by physical manipulation with the designed tool or by applying a heat source. The heat source can include the bone or other sources of body heat when the transition temperature is set to be at body temperature. For example, when the clip is made of a shape memory alloy having a transition temperature set to be body temperature, at surgery the clip is first cooled and reshaped to obtain the ideal shape for application: the diamond at the bridge closed widthwise, legs extending perpendicularly from the bridge and a concavity in the bridge. After the staple's legs are placed into respective bores drilled in the bone fragments to be fused together, the staple is driven deep into the bone with a percussion tool. Once the legs of the staple are in the bone, the body temperature of the bone warms the staple, reverting its shape to the original manufactured shape. A compressive force is progressively developed between the legs. At this point, if there has been too much compression and the insertion tips of the legs have bent away from each other, corrective positioning can be achieved by applying an upward force to the depression in the bridge with the insertion tool. Proper planning and selection of a clip with a final shape which will compress the same distance as the gap between bone fragments may also avoid the need for additional use of tools and corrective measures.

It is another object of the present invention to provide an improved insertion tool to insert an osteosynthesis clip into bone fragments. The improved tool incorporates an adjustable member configurable to contact the bridging portions of the clip. This contact is necessary to insert the clip into bores drilled for receiving the engagement legs and for applying the third force opposite to the second force applied to the non-linear deformable region. By incorporating the adjustable member to the improved tool, it is capable of correctly applying the third force to the bridge member of a stepped clip having a shape exemplified in FIGS. 4a and 4b of the '600 App. and can be easily reconfigured to also engage and apply the third force to the bridge at points nearest the respective bridging portions of a non-stepped ("U"-shaped) clip as shown in FIGS. 1 and 2 of the '600 App.

BRIEF DESCRIPTION OF THE DRAWINGS

FIGS. 6a through 6d comprising FIGS. 6A.1, 6A.2, 6B.1, 6B.2, 6C.1, 6C.2, 6D.1 and 6D.2 show an operational sequence for inserting and the improved osteosynthesis in order to bring together two otherwise separate bone fragments;

DETAILED DESCRIPTION

Figure 1:
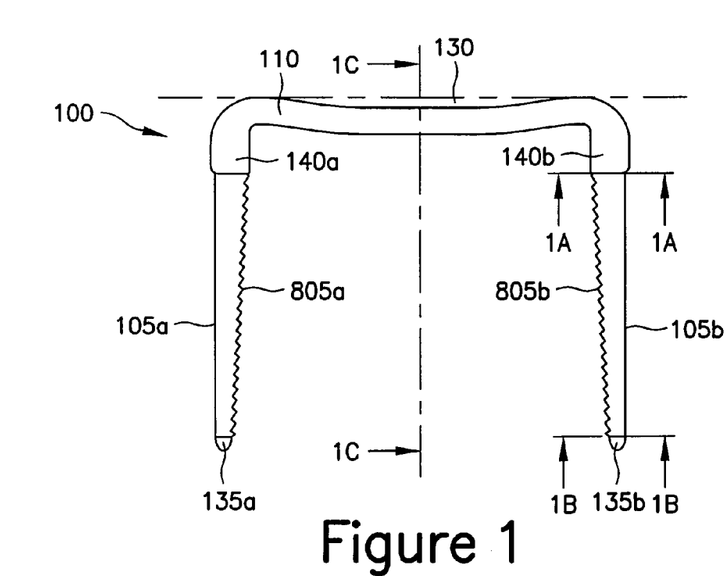
FIG. 1 and FIGS. 1A to 1D illustrate top, side and cross sectional views of a first exemplary non-stepped osteosynthesis clip according to the present invention having engagement legs with a planar surface having threaded grips extending fully along the planar surface opposite a rounded tapered surface.
Figure 1A:
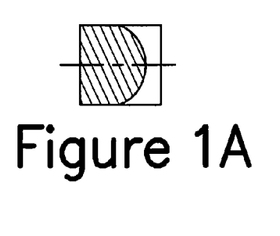
Figure 1B:
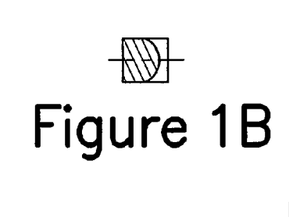
Figure 1C:
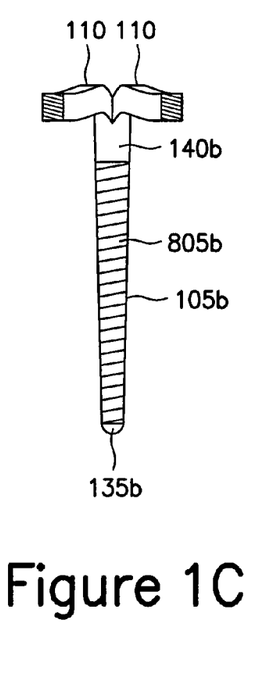
Figure 1D:
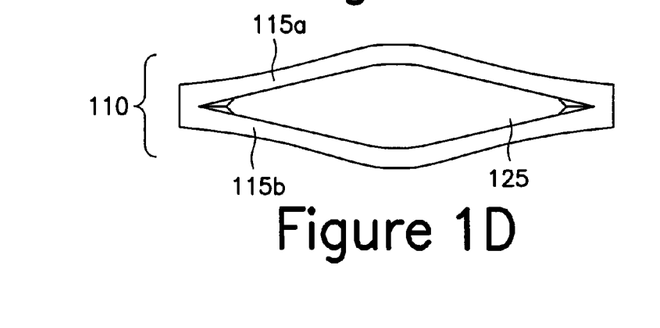

To the extent that the elements of the invention match those represented in the '600 App., the reference numerals will remain the same. Referring now to FIG. 1, there are seen side, top and a cross sectional views along drawn lines "A-A", "B-B" and "C-C", respectively, of a first exemplary improved, elastic, osteosynthesis clip 100 according to the present invention. Clip 100 includes at least two engagement legs 105a and 105b and a connecting bridge 110 to couple engagement legs 105a, 105b to one another, thereby forming a unitary clip 100. Engagement legs 105a, 105b extend approximately parallel to one another and include respective insertion tips 135a, 135b, shown to be rounded, for insertion into the bone tissue and respective bridging tips 140a, 140b coupled to bridge 110. A taper may be provided in the engagement legs 105a, 105b by having a linear decrease in cross sectional area along the distance between the bridging tips 140a, 140b to respective insertion tips 135a, 135b. This taper is shown by the comparingly decreased cross sectional area of the legs 105a, 105b along line B-B, nearest insertion tips 135a, 135b, as compared to that along line A-A, nearest bridging tips 140a, 140b, as shown in FIGS. 1 through 4.

Figures 2, 2A, 2B, 2C, 2D:
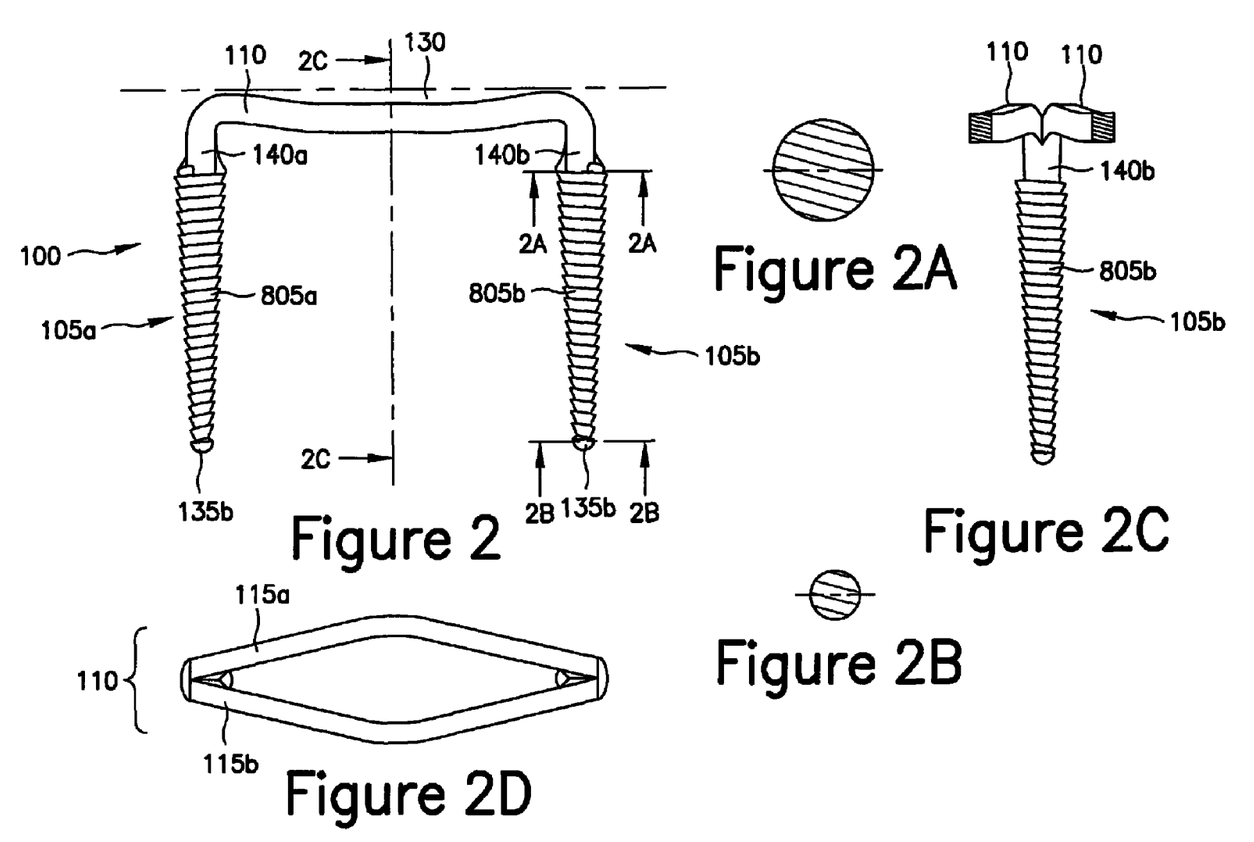
FIG. 2 and FIGS. 2A to 2D show top, side and cross sectional views of a second exemplary non-stepped osteosynthesis clip according to the present invention having tapered engagement legs that are circular in cross section and have a threaded gripping surface extend fully along a circumference and length of the circular surface of the engagement legs.
Figures 3, 3A, 3B, 3D:
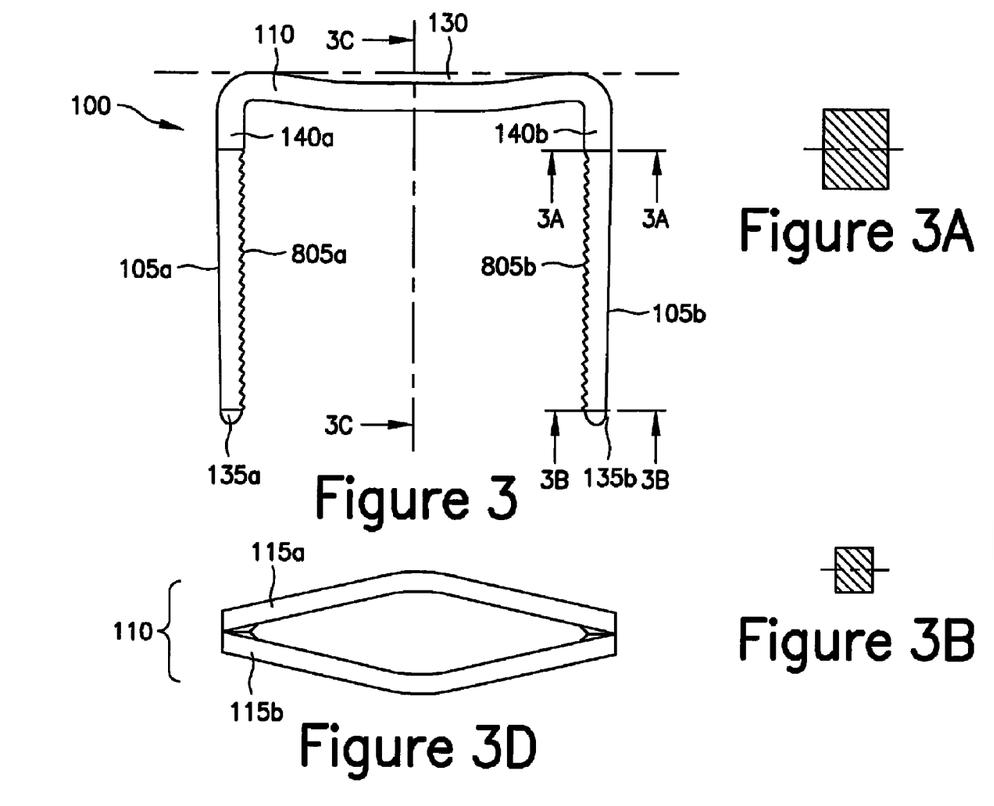
FIG. 3 and FIGS. 3A to 3D illustrate top, side and cross sectional views of a third exemplary non-stepped osteosynthesis clip according to the present invention having tapered engagement legs that are square in cross section and having a threaded gripping surface extending fully along at least one planar surface of the engagement legs.
Figure 3C:
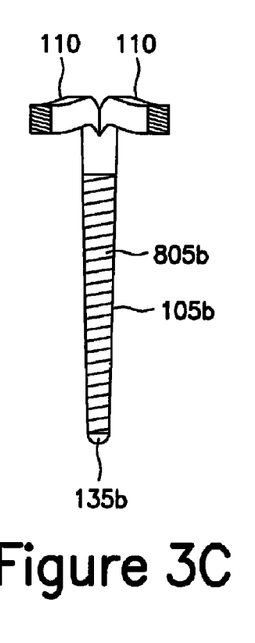
Figure 4:
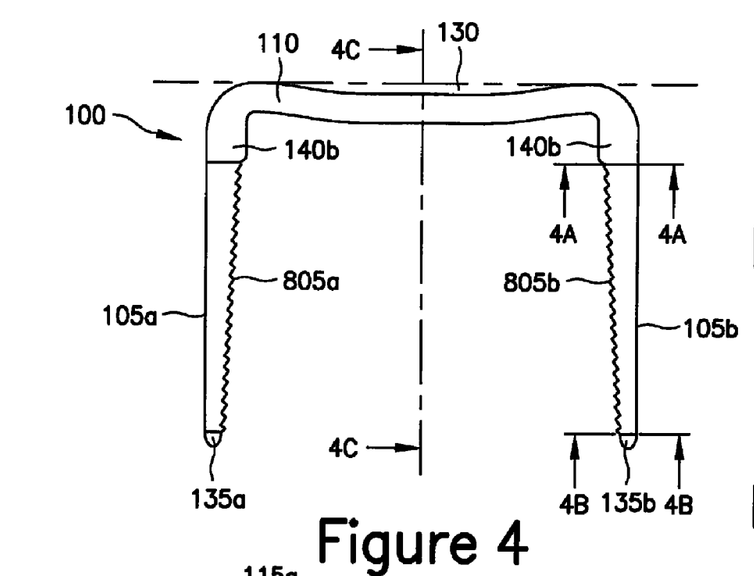
FIG. 4 and FIGS. 4A to 4D show top, side and cross sectional views of a forth exemplary non-stepped osteosynthesis clip according to the present invention having the threaded gripping surface extending fully along a rounded surface of otherwise square tapered engagement legs.
Figures 4A, 4B, 4C:
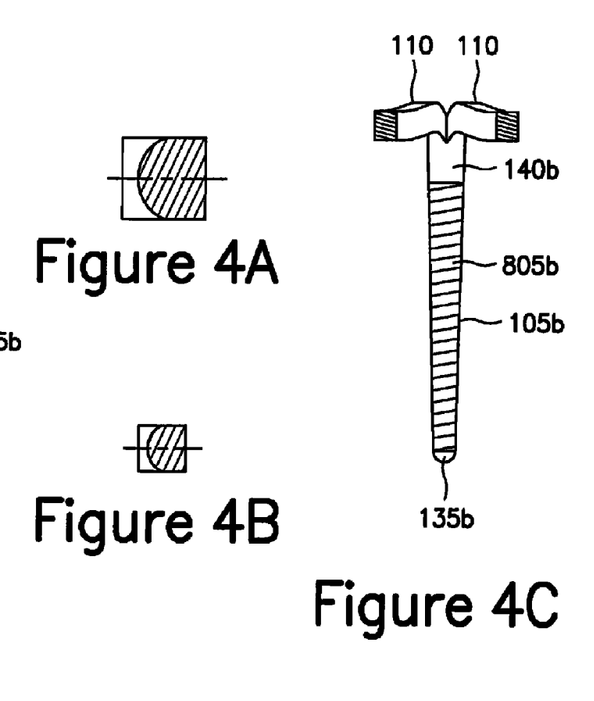
Figure 4D:
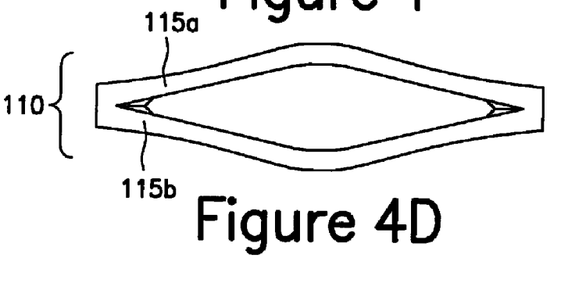

Engagement legs 105a, 105b may have any cross sectional shape (e.g., round, square or any combination of the two) suitable for insertion into the bore holes drilled in the bone segments. Furthermore, all none or some of the sides of legs 105a, 105b may taper. For example, FIG. 1 illustrates the cross section of legs 105a, 105b to have three straight sides and one rounded side, the straight side positioned opposite the rounded side faces toward the other leg 105a or 105b and is provided with a respective gripping surface 805a, 805b for frictionally engaging bone tissue. In this embodiment, all sides taper. As shown in FIG. 2, the cross section of legs 105a, 105b is circular and tapered around the entire circumference. The entire circumference is also provided with a threaded screw-like gripping surface 805a, 805b for frictionally engaging bone tissue. This embodiment creates minimal or no cutting during the removal process because the later portions of the legs 105a, 105b to be removed are narrower than respective bridging tips 140a, 140b. Also, legs 105a, 105b which have a circular circumference can also not be tapered (not illustrated). As such, upon removal the screw-like threads would follow the path carved by threads closer to the bridging tip 140a, 140b throughout the entire removal process. FIG. 3 illustrates the cross section of legs 105a, 105b to have four straight or planar sides and only one of the four sides being provided with respective threaded screw-like gripping surface 805a, 805b. In this embodiment, inward sides of the legs that face each other are facing each other are provided with the threaded screw-like gripping surface 805a and 805b for frictionally engaging bone tissue. All sides except those sides having the gripping surface 805a, 805b taper. FIG. 4 illustrates the cross section of the legs 105a and 105b to have three straight sides and one rounded side, the rounded sides of each leg are positioned on the inward side facing the other leg 105a or 105b and is provided with a gripping surface 805a and 805b for frictionally engaging bone tissue. The taper of the legs 105a, 105b can again be seen in by comparing the cross sectional views along lines A-A" and "B-B".

The gripping surfaces 805a, 805b of the improved clip 100 (e.g., gripping teeth, threads, ridges) are provided along substantially an entire distance between the insertion tip 135a, 135b and respective bridging portions 140a, 140b of the engagement legs 105a, 105b. In the present invention, the gripping teeth 805a, 805b resemble screw threads having a sloped or inclined trace along the engagement legs 105a, 105b. In this exemplary embodiment, engagement legs 105a, 105b are provided with helical screw surfaces 805a, 805b, which advantageously facilitate the removal of clip 100 after the bone tissue (not shown) has been fused. For this purpose, clip 100 may be cut in the locations of bridging tips 140a, 140b to remove bridge 110, as shown in FIG. 8b of the '600 App. Once bridge 110 is removed, engagement legs 105a, 105b may be removed from the bone tissue, for example, by unscrewing engagement legs 105a, 105b in a counterclockwise direction 860a, 860b, as shown in FIG. 8c. Of the '600 App. The helical screw surfaces 805a, 805b in the present invention are advantageous to prior art devices because the threads in the present invention are provided along substantially an entire distance between respective bridging tips 140a, 140b and the insertion tips 135a, 135b thereby minimizing the amount of bone that must be cut when removing the legs 105a, 105b from the fused bone. This results in a maximum cutting distance required of one 360 degree turn of either leg 105a, 105b when only one side of legs 105a, 105b is threaded as described above. Likewise, a leg 105a, 105b having a circular cross section and threaded along the entire circumference of legs 105a, 105b results in a minimum cutting upon exit. In fact, little to no cutting will be necessary upon exit if the legs 105a, 105b are circular and the helical screw-like gripping surface and the length of the legs 105a, 105b covered with the helical gripping surface is equal to or greater than the depth to which the clip is inserted into the bone fragments.

Figure 5:
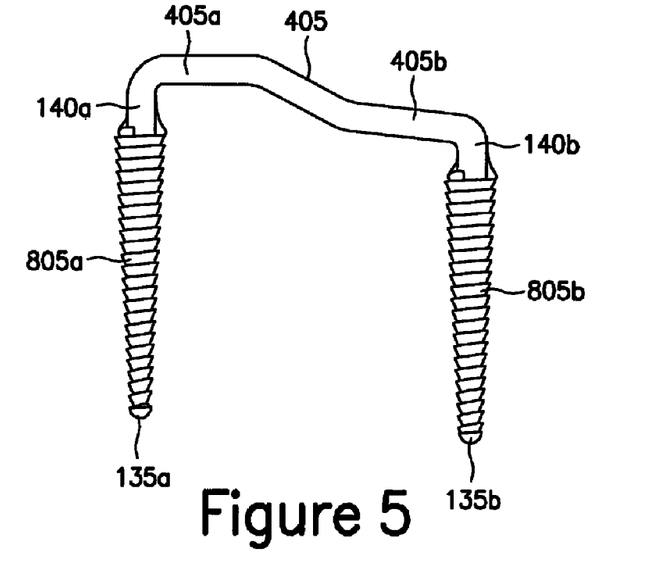
FIG. 5 and FIGS. 5A to 5B illustrate top and side views a fifth exemplary stepped osteosynthesis clip according to the present invention having a stepped bridge and tapered engagement legs that are circular in cross section and have a threaded gripping surface extend fully along a circumference and length of the circular surface of the engagement legs.
Figure 5A:
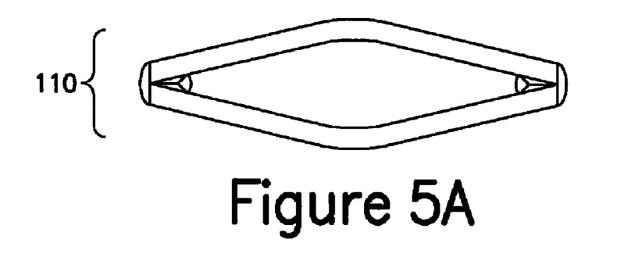
Figure 5B:
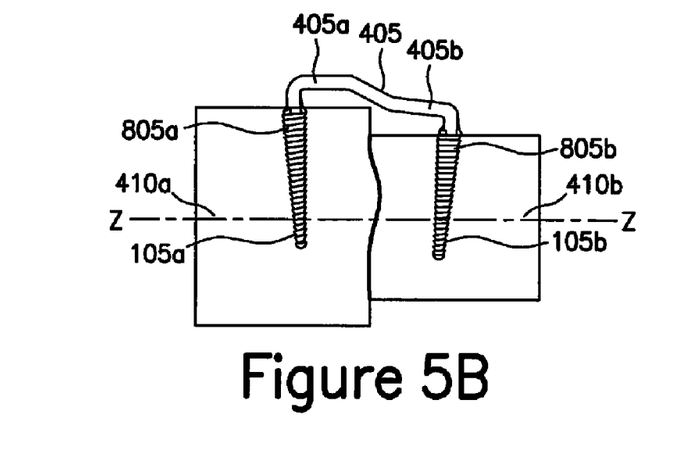

Bridge 110 includes two elongated sections 115a, 115b extending along side one another. The sections 115a, 115b include respective bulges 120a, 120b, which together form a space of separation 125 between elongated sections 115a, 115b. As shown in FIG. 1 the space of separation 125 is shown in the form a diamond shape. Elongated sections 115a, 115b may also extend side by side one another along a non-linear trajectory, thereby forming a non-linear deformable region 130, such as a depression 130, as may be seen in the side view of FIGS. 1-4. Deformable region 130 is provided to facilitate clamping of bone tissue fragments (not shown), as more fully described below. Elongated sections 115a, 115b of bridge 110 may also be provided with a stepped section 405, as shown in FIG. 5. In this manner, the stepped section 405 creates a stepped-up region 405a and a stepped-down region 405b. As such, the clip 100 may be used to set bone fragments 410a, 410b having varying diameters, so that the axes of bone fragments 410a, 410b align with one another, as shown in FIG. 5. The engagement leg 105a extending from stepped-up region 405a is received by a bone fragment 410a having a large diameter and leg 105b extending from stepped-down region 405b is received by a second bone fragment 410b having a small diameter when compared to bone fragment 410a. Because the clip 100 is stepped by stepped section 405, it aligns the bone fragments of different diameter 410a, 410b along their central linear axis "Z-Z". Referring to further to FIG. 5, it can be seen that clip 100 has engagement legs 105a, 105b having respective tapered circular cross sections and threaded screw-like gripping surfaces 805a, 805b along the entire circumference of the legs 105a, 105b between the insertion and bridging tips, respectively 135a to 140a and 135b to 140b for frictionally engaging bone tissue 410a, 410b.

The clip 100 may be made of any material suitable for insertion into living tissue (e.g., bone tissue). For example, clip 100 may be made of a biocompatible material (e.g., stainless steel alloy or a titanium alloy metal such as TA6V of medical grade) having suitable elasticity and mechanical strength. Additionally, the improved clip 100 may be made of shape memory alloys. Manufacturing the improved clip 100 with shape memory alloys allows for the separation of the elongated sections 115a, 115b without use of an instrument and/or a separate tool. Rather, the reconfiguration of the clip 100 results from heat treatment as will be described in the process described below.

Figure 6A:
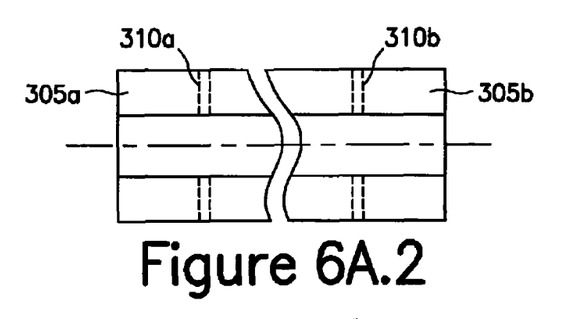
Figure 6A:
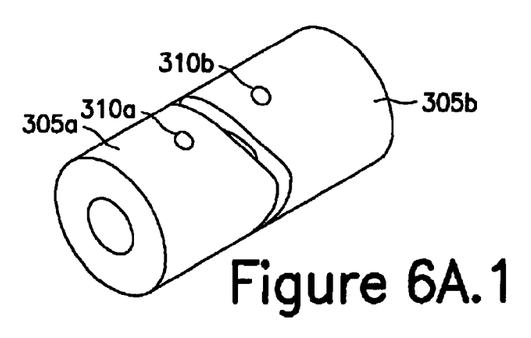
Figure 6B:
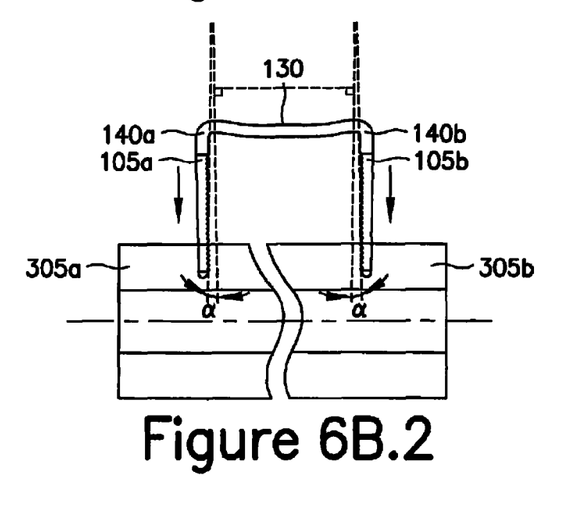
Figure 6B:
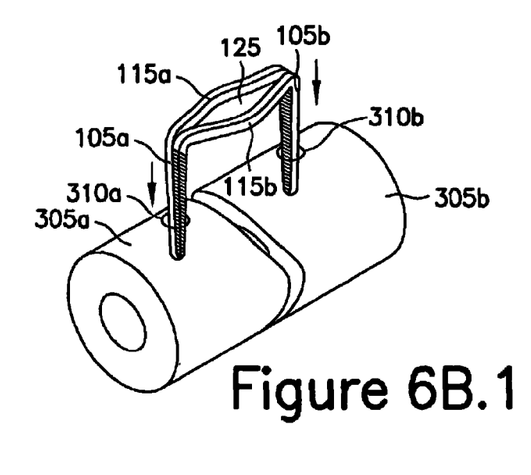

Referring now to FIGS. 6a through 6d, there is seen an operational sequence for inserting osteosynthesis clip 100 with a depression 130 to couple bone tissue fragments 305a, 305b. As shown in FIG. 3a, bone fragments 305a, 305b are pre-drilled with respective clip reception holes 310a, 310b for respectively receiving engagement legs 105a, 105b of osteosynthesis clip 100. After drilling holes 310a, 310b, osteosynthesis clip 100 is inserted into bone tissue fragments 305a, 305b, as shown in FIG. 6b. For this purpose, clip 100 may be coupled to an instrument (not shown), and a percussion force may be applied to the instrument (not shown) to drive clip 100 into bone tissue fragments 305a, 305b. Once clip 100 is fully inserted into bone tissue fragments 305a, 305b, a first force is applied to elongated sections 115a, 115b thereby separating them from each other. This is done with a tool, for example, by the known instrument and/or a separate tool (not shown), as shown in FIG. 6c or by thermally altering the clip that consists of a shape memory alloy.

Figure 6C:
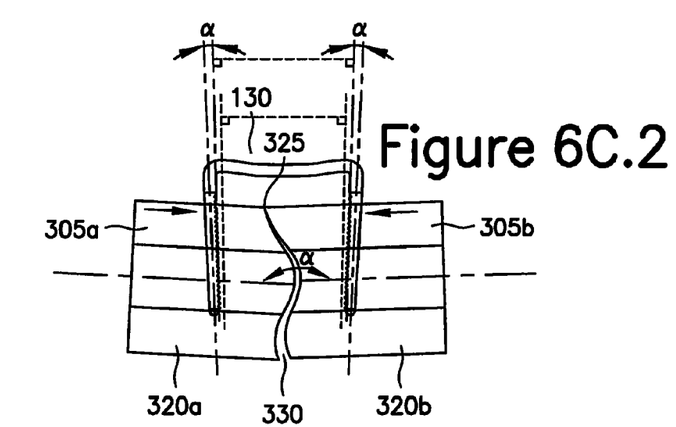
Figure 6C:
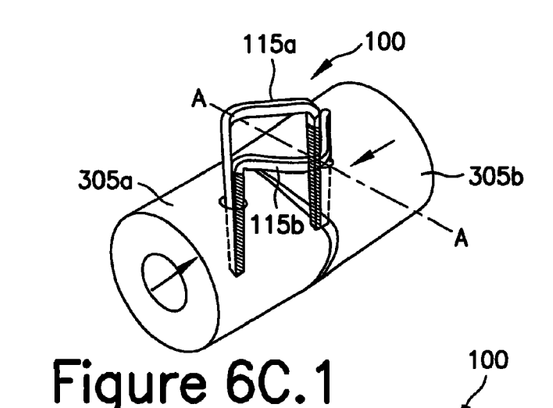

If the clip 100 is constructed of a shape memory alloy having a transition temperature, the clip chosen for use in the operation will have engagement legs 105a, 105b arranged a distance from each other equal to a desired distance between the drilled bore holes 310a, 310b after the surgery is complete. Then, before insertion, the clip 100 is cooled to a temperature below its transition temperature. The clip 100, while cooled, is then lengthened along the bridge 110 by compressing the elongated members 115a, 115b together and thereby eliminating the bulge 125 and driving the engagement legs 105a, 105b further away from each other until the legs align with the pre-drilled holes. The clip 100 is inserted into holes 310a, 310b as described above. Clip 100 is then heated to its transition temperature or above the transition temperature thereby causing the first force on elongated members 115a, 115b to separate and causing the clip 100 to return to its manufactured shape and moving the engagement legs 105a, 105b toward each other, resultantly compressing the two bone fragments. For example, if the clip 100 is made with a shape memory alloy having a transition temperature at or less than the average human body's temperature, approximately 97 to 100 degrees Fahrenheit, 36 to 38 degrees Celsius, during the cooling process clip 100 would be cooled below such a temperature (with ice, liquid ice or other cooling agent) and deformed into an extended shape as described above before insertion. This allows the user (i.e., doctor) to align the engagement legs 105a, 105b with respective bores 310a, 310b as they are positioned before surgery or fusion. Once inserted, as described above, the body temperature of the bone or surrounding tissue warms clip 100 to or above its transition temperature, reverting the clip to its original manufactured shape. The original manufactured shape being with the space 125 of clip 100 widened along line A-A as seen in FIG. 6c. Therefore, heating the clip 100 caused engagement legs 105a, 105b to approach one another resulting in bone fragments 305a, 305b to come in contact with one another under pressure. In the above stated example, the bone fragments themselves were the heat source. Other potential heat sources include, but are not limited to, a blow drier, an electrical current or saline solution. It is worth noting that human tissue can be damaged if brought to temperatures above 42 degrees Celsius, therefore, it is not recommended that the transition temperature of the clip 100 be set at 42 degrees Celsius or higher. Also, if the bone fragments 305a, 305b do happen to come in contact with one another under too high a pressure, elongated sections 115a, 115b may also be brought closer together with manual manipulation or tooling. This causes space 125 of clip 100 to narrow along line A-A, thereby causing engagement legs 105a, 105b to separate from one another.

If elongated sections 115a, 115b are over-separated (i.e., separated too much), for example, by a surgeon applying too much separation force on elongated sections 115a, 115b, the contact pressure between bone tissue fragments 305a, 305b in an area near the top surfaces 315a, 315b of bone tissue fragments 305a, 305b may exceed the contact pressure between bone tissue fragments 305a, 305b in an area near the bottom surfaces 320a, 320b of bone tissue fragments 305a, 305b. A similar effect may occur if the clip 100 constructed of a shape memory alloy selected by the doctor was too small resulting in engagement legs 105a, 105b coming too close to each other and thereby creating too strong of a compression between bone fragments 305a, 305b. This excessive force may cause bone tissue fragments 305a, 305b to pivot upwardly about contact pivot surface 325, thereby causing insertion tips 135a, 135b of engagement legs 105a, 105b to pivot away from one another about bridging tips 140a, 140b, as seen in FIG. 6c. In this manner, the longitudinal axes of the bone tissue fragments 305a, 305b become unaligned and a gap 330 forms between the fragments 305a, 305b. In this case, merely bringing elongated sections 115a, 115b closer together to separate bone tissue fragments 305a, 305b may not help alleviate the problem.

Figure 6D:
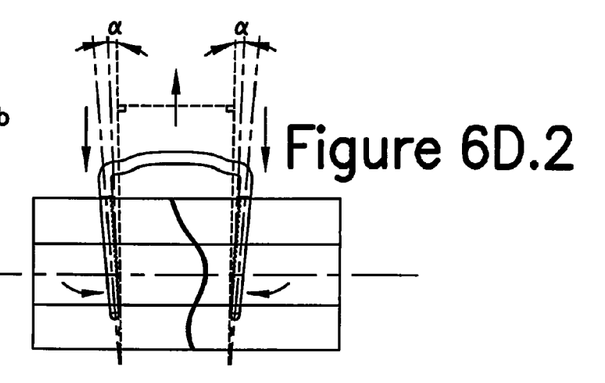
Figure 6D:
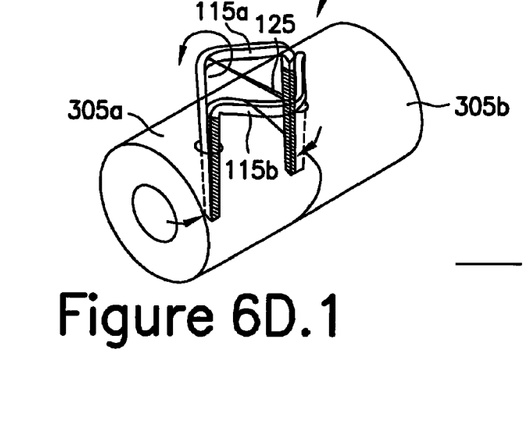

To close gap 330 and to ensure proper setting of bone tissue fragments 305a, 305b, a second force, such as an upward force, is applied to elongated sections 115a, 115b of clip 100 in an area of non-linear deformable region 130, as shown in FIG. 6d. While applying the second force to elongated sections 115a, 115b, withdrawal of clip 100 may be prevented by simultaneously applying an opposing third force, such as a downward force, on bridging tips 140a, 140b. The second force applied to elongated sections 115a, 115b of clip 100 causes at least a partial linearization of non-linear deformable region 130. This causes insertion tips 135a, 135b to pivot toward one another about bridging tips 140a, 140b, thereby causing gap 330 to close between the bottom surfaces 320a, 320b of bone tissue fragments 305a, 305b, as shown in FIG. 6d.

Figures 7, 7A, 7B:
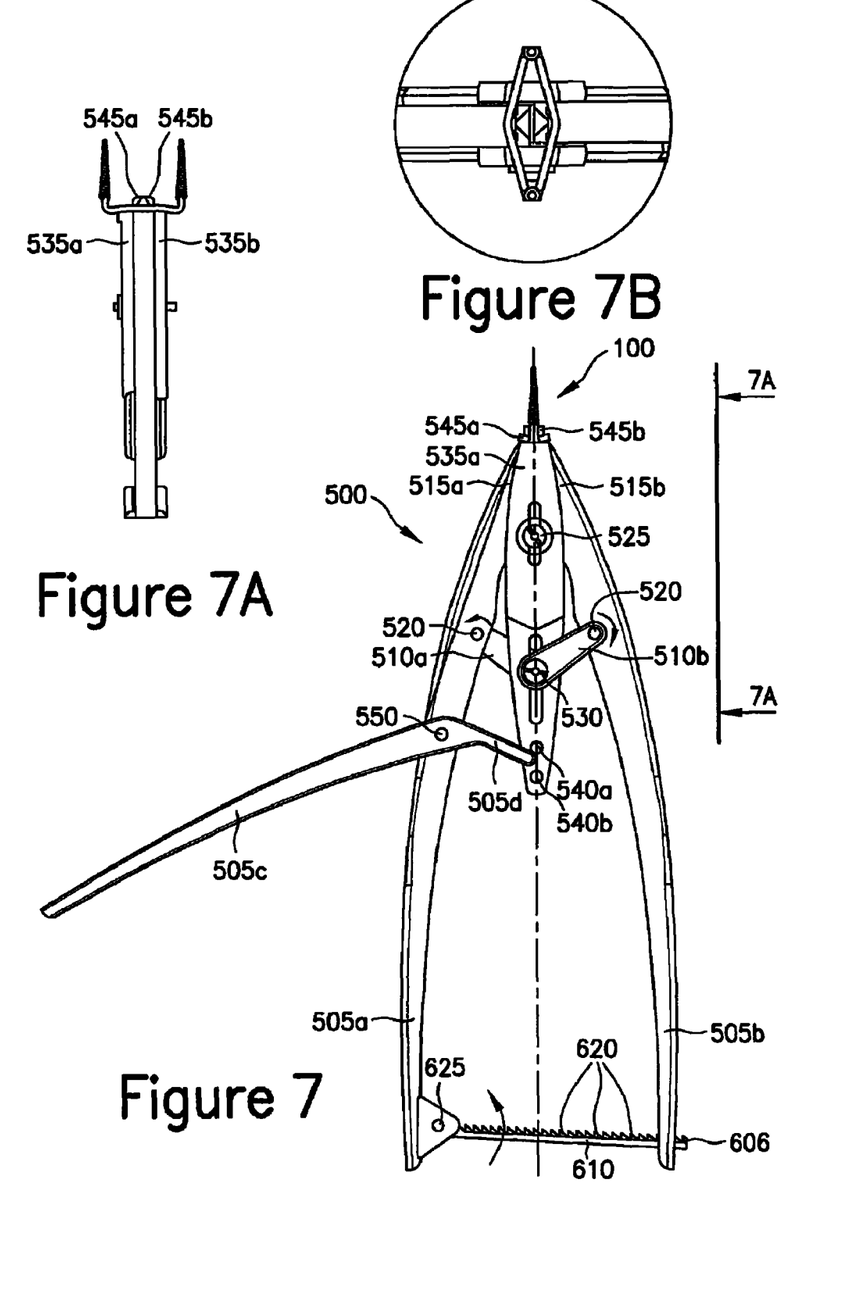
FIG. 7 and FIGS. 7A and 7B illustrate a first exemplary fixation tool as presently known in the art.
Figures 8, 8A, 8B:
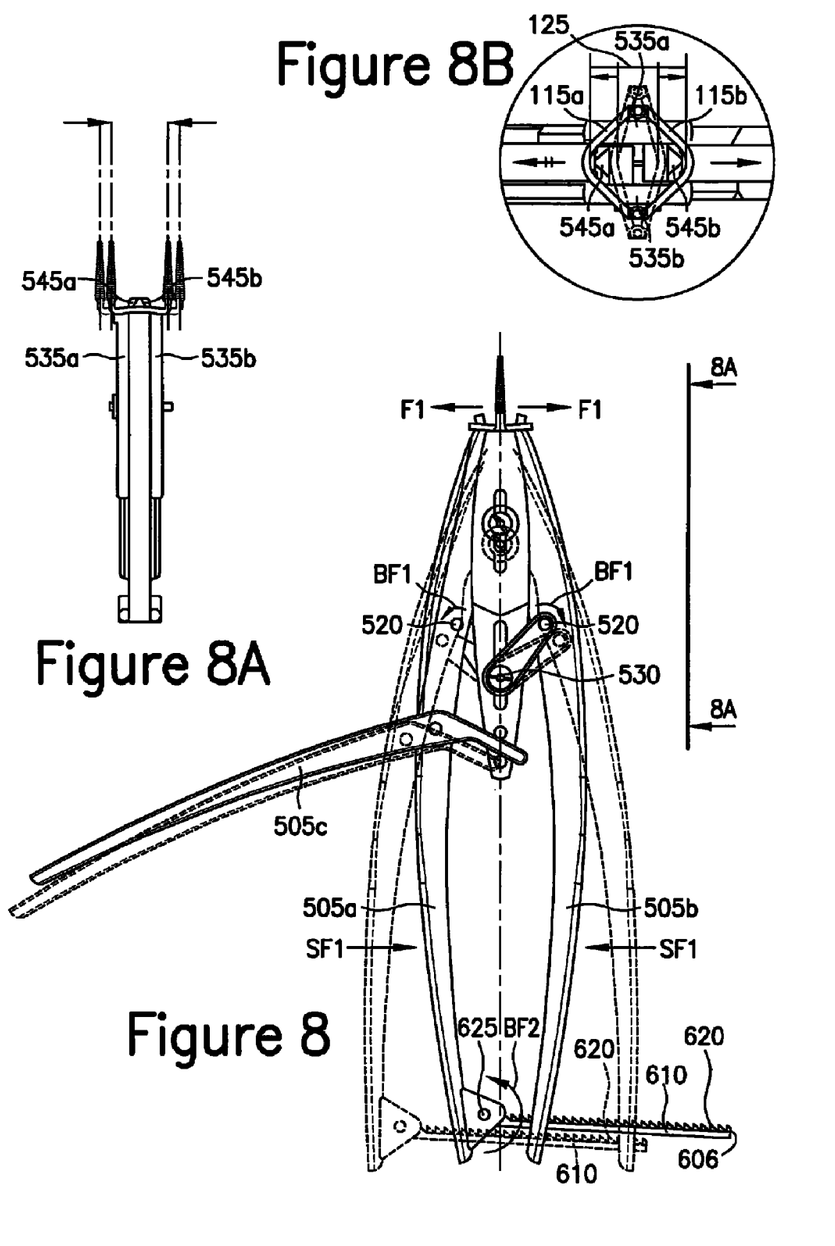
FIG. 8 and FIGS. 8A and 8B show an operational sequence for compressing the engagement legs toward each other by contracting the exemplary fixation tool as presently known in the art.
Figures 9, 9A, 9B:
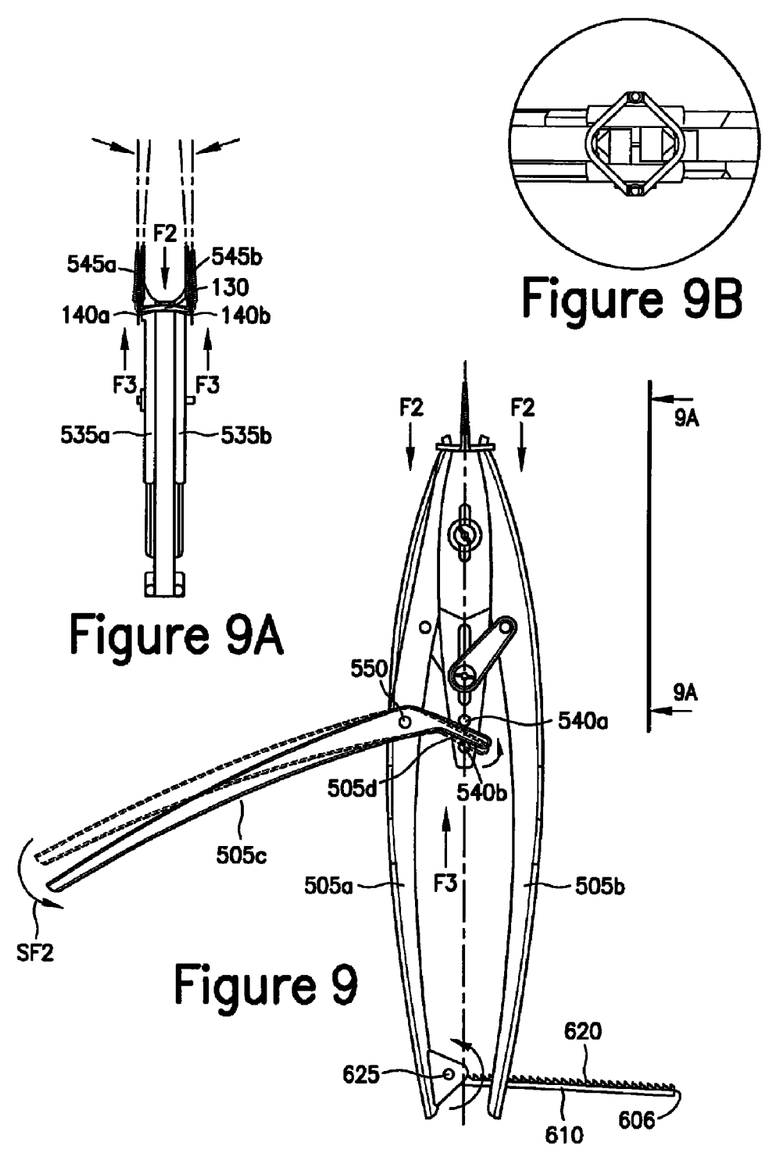
FIG. 9 and FIGS. 9A and 9B illustrate an operational sequence for compressing the insertion tips of the engagement legs toward each other by applying a force to the non linear bridge with the exemplary fixation tool known in the art.

Referring now to FIGS. 7 through 10, there is seen a first exemplary fixation tool 500 configured to insert clip 100 into bone tissue fragments 305a, 305b, apply the first force to separate the elongated sections 115a, 155b, apply the second force to the non-linear deformable region 130 and to apply the third force to the bridge 110 near the bridging tips. The fixation tool 500 may be in any of the many known forms as described in the known art incorporated by reference above. One exemplary embodiment of the fixation tool 500, as shown in FIGS. 7 through 9 includes handles 505a, 505b, a set of engagement arms 515a, 515b respectively coupled to handles 505a, 505b, pivot arms 510a, 510b respectively and pivotally coupled to handles 505a, 505b, a first biasing arrangement 520 (e.g., a pair of biased spring clips, a spring, etc.) Creating biasing force BF1 configured to bias handles 505a, 505b in a normally opened position, a guiding bolt 530 coupled to pivot arms 510a, 510b, a pair of pushing plates 535a, 535b slidably coupled to guiding bolt 530 and having a set of pushing pins 540a, 540b respectively, a spacing bolt 525 slidably coupled to the pushing plates 535a, 535b and extending between and separating the engagement arms 515a, 515b, a handle 505c is pivotally coupled to handle 505a having a lever 505d for pushing against pushing pins 540a, 540b, a rachet clip 610 having teeth 620 is pivotally connected to handle 505a via a second biasing means 625 (i.e. spring coil, spring clip, etc.) Configured to create a second biasing force BF2 causing the teeth 620 to engage an end of handle 505b near distal end 606 of clip 620.

Fixation tool 500 may be used to perform the operational sequence shown in FIGS. 6a through 6d for inserting osteosynthesis clip 100 to couple bone tissue fragments 305a, 305b. After drilling holes 310a, 310b, osteosynthesis clip 100 is inserted into bone tissue fragments 305a, 305b, for example, using fixation tool 500. For this purpose, engagement arms 515a, 515b are provided with respective engagement flanges 545a, 545b for fixedly engaging elongated sections 115a, 115b between pushing plates 535a, 535b. Once clip 100 is coupled to fixation tool 500 between flanges 545a, 545b and respective pushing plates 535a, 535b, osteosynthesis clip 100 is inserted into bone tissue fragments 305a, 305b, as shown in FIG. 6b. For this purpose, a percussion force, for example, may be applied to handles 505a and/or 505b or to pushing plates 535a, 535b to drive clip 100 into bone tissue fragments 305a, 305b. Alternatively, it should be appreciated that clip 100 may be inserted into bone tissue fragments 305a, 305b using a separate tool and/or percussion instrument, such as a surgical hammer.

Once clip 100 is fully inserted into bone tissue fragments 305a, 305b, the first separating force "F1" may be applied to elongated sections 115a, 115b in order to separate them from one another and cause bone tissue fragments 305a, 305b to contact one another under pressure. For this purpose, a user, for example, a surgeon, applies a first-squeezing-force to handles 505a, 505b, as shown by arrows named "SF1", against the biasing force of first biasing arrangement 520, as shown in FIG. 8. This creates the first force F1 from the engagement flanges 545a, 545b on engagement arms 515a, 515b, causing them to separate from one another. Accordingly, this causes space 125 of clip 100 to widen, thereby causing engagement legs 105a, 105b of clip 100 to approach one another and to cause bone tissue fragments 305a, 305b to come in contact with one another under pressure. The teeth 620 on the ratchet clip 610 are driven into handle 505b by second biasing force BF2 created by second biasing member 625 thereby preventing the handles 505a, 505b form separating and maintaining the first force on the elongated members 115a, 115b of the clip 100.

As shown in FIG. 9, without releasing the rachet clip 610 from handle 505b the user (e.g., the surgeon) then applies a second-squeezing-force "SF2" to handles 505a, 505c pushing lever 505d against pushing pin 540a thereby applying the third force F3 along the pushing plates 535a, 535b and against the bridge 110 near the bridging tips 140a, 140b. Also, the equal an opposite second force F2 is applied on the non-linear deformable region 130 of the clip 100 via engagement flanges 545a, 545b.

As the user (e.g., the surgeon) continues to apply the second-squeezing-force SF2 to handles 505a, 505c, pushing plates 535a, 535b apply a downward force F3 to bridging tips 140a, 140b of clip 100, while engagement flanges 545a, 545b apply an upward force F2 to elongated sections 115a, 115b of clip 100 in an area of non-linear deformable region 130, as shown in FIG. 6d. As described above, the second force F2 (e.g., an upward force) applied to elongated sections 115a, 115b of clip 100 causes at least a partial linearization of non-linear deformable region 130 (e.g., non-linear depression 130). This causes insertion tips 135a, 135b to pivot toward one another about bridging tips 140a, 140b, thereby causing gap 330 to close between the bottom surfaces 320a, 320b of bone tissue fragments 305a, 305b, as shown in FIG. 6d. The same may be achieved with the use of a dome forming the non-linear deformable region 130 as described in the '600 App. and second and third forces being opposite to the currently applied forces.

Figures 10, 10A:
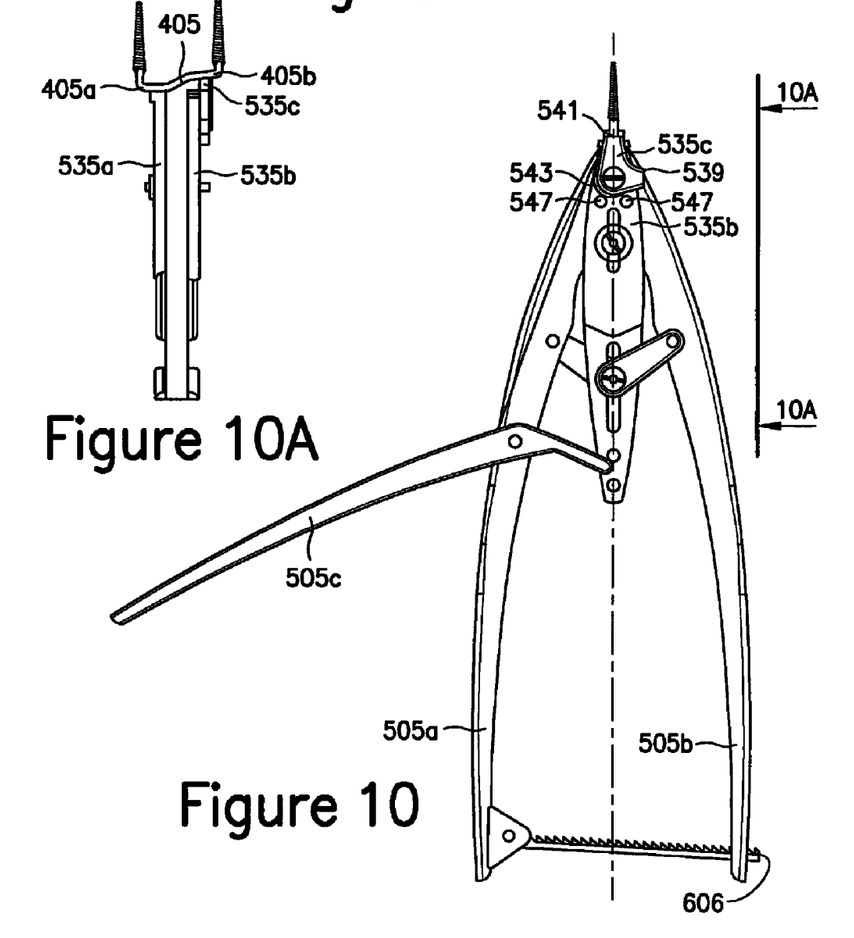
FIG. 10 and FIGS. 10A and 10B show an exemplary fixation tool having an adjustable engagement member for accommodating either stepped and non stepped osteosynthesis clips in accordance with the present invention.
Figure 10B:
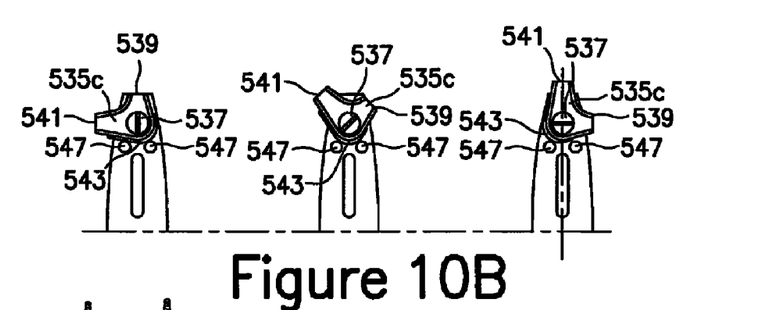

However, when the elongated sections 115a, 115b of bridge 110 are provided with a stepped section 405 this creates a stepped-up region 405a and a stepped-down region 405b for joining bone section having different diameters 410a, 410b. The creation of a stepped down region 405b requires a long pushing member to engage the bridging tip 140b and a short bridging member 535a to contact the stepped up region 405a so that the third force F3 can be evenly applied to both sides of the bridge 110. It is further advantageous if fixation tool 500 is adaptable for either engaging a standard "U" shaped clip as depicted in FIGS. 1-4 or for engaging a stepped-clip as seen in FIG. 5. To solve this problem, the fixation tool 500 is further provided with an adjustable pushing plate 535c, as shown in FIG. 10 to be coupled to pushing plate 535b. Therefore pushing plate 535a and 535b remain equally sized for engaging a standard "U" shaped clip 100 as seen in FIGS. 1 through 4. However, if necessary to engage a stepped down region 405b, the fixation tool 500 is further provided an adjustable pushing plate 535c adjustably mounted to pushing plate 535b. While many different configurations may be achieved, a simple and cost effective example of the adjustable pushing plate 535c is shown to be an "L" shaped planar member having short side 539 and long side 541. The distal ends of the long and short sides, respectively 541, 539, being contact surfaces for applying the third force F3 to the bridging tips 140a, 140b of clip 100. The adjustable member 535c being pivotally mounted by pin 537 to pushing plate 535b. Accordingly, the adjustable pushing member can be places in an extended position by rotating the adjustable pushing plate until the long end 541 extends beyond pushing plate 535b toward engagement member 545b. The adjustable pushing member 535c is placed in a retracted position by rotating the adjustable pushing member 535c until the short side 539 extends toward the engagement member 545b. Accordingly, when the short end 539 of member 535c is aligned toward the engagement member 545b then the fixation tool 500 is configured to engage a traditionally "U" shaped clip 100 as illustrated in FIG. 1-4. When the long end 541 of member 535c is aligned toward the engagement member 545b, then the fixation tool 500 is configured to engage the stepped down region 405b of a clip 100 as shown in FIG. 5 and FIG. 10. A third biasing arrangement 543 may also be included to ensure that the adjustable pushing member 535c does not freely rotate, but rather is only released form a designated position when a predetermined rotational force is applied to the adjustable pushing plate 535c, thereby allowing the adjustable pushing plate 535c to be locked between the extended and retracted settings as described above. For example, the fourth biasing member 543 may include a spring 543 extending from the adjustable pushing member 535c and a set of locking pins 547 extending form pushing plate 535b. The locking pins 547 are arranged to require exerted force to transfer between the extended and retracted positions.

After the second-squeezing-force is applied to handles 505a, 505c and clip 100 is properly inserted into bone tissue fragments 305a, 305b, handle 505b is released from teeth 620 of ratchet clip 510 by applying a releasing force at the ratchet clip's distal end 606 contrary to second biasing force BF2. For this purpose, the user (e.g., the surgeon) applies a force to end 606 of ratchet clip 610 in a direction against the biasing force of second biasing arrangement 625. In this manner, teeth 620 of ratchet clip 610 disengage the bottom end of handle 505b, thereby permitting handles 505a, 505b to separate from one another via the biasing force produced by first biasing arrangement 520.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An improved osteosynthesis clip for the cicatrization of bone tissue fragments, the clip comprising:
    at least two engagement legs extending approximately parallel to one another and including respective tip portions to be inserted into the bone tissue fragments;
    a connecting bridge coupled to portions of the at least two engagement legs opposite the tip portions and comprising the same material as the engagement legs, the connecting bridge including at least two elongated sections extending along side one another, the elongated sections extending along a non-linear trajectory to form a non-linear deformable region;
    the elongated sections of the connecting bridge having top surfaces for receiving percussion blows to allow the engagement legs to be hammered into the bone tissue fragments; and
    wherein the engagement legs have respective helical screw surfaces extending along substantially an entire distance between respective tip portions and respective opposite portions to facilitate removal of the clip after the bone tissue fragments have fused and the connecting bridge is severed;
    wherein the at least two engagement legs have tapering cross sectional areas that continuously decrease as they extend from the bridge toward the tip portions along substantially an entire distance between the bridge and the tip portions.

2. The osteosynthesis clip of claim 1, wherein the engagement legs and the connecting bridge are constructed from a biocompatible material.

3. The osteosynthesis clip of claim 1, wherein the non-linear deformable region includes one of a depression and a dome.

4. The osteosynthesis clip of claim 1, wherein the two elongated sections include respective bulges that together form a space of separation between elongated sections.

5. The osteosynthesis clip of claim 1, wherein the elongated sections include respective stepped-up sections to permit the setting of bone fragments having varying diameters.

6. The osteosynthesis clip of claim 1, wherein the at least two engagement legs have at least one straight side.

7. The osteosynthesis clip of claim 1, wherein the at least two engagement legs have at least one rounded side, are circular in cross section or are square in cross section.

8. The osteosynthesis clip of claim 1, wherein only one side of each of the at least two engagement legs have respective helical screw surfaces extending along substantially an entire distance between respective tip portions and respective opposite portions.

9. The osteosynthesis clip of claim 1, wherein at least the connecting bridge is constructed from a shape memory alloy or thermo-sensitive alloy having a transition temperature, whereby any deformation to the shape memory alloy after being manufactured can be reversed by heating the shape alloy metal to a second temperature equal to or greater than the transition temperature.

10. The osteosynthesis clip of claim 9, wherein the transition temperature is no greater than 42 degrees Celsius.

11. The osteosynthesis clip of claim 9, wherein the transition temperature is no greater than 38 degrees Celsius and no less than 36 degrees Celsius.

12. The osteosynthesis clip of claim 9, wherein the non-linear deformable region includes one of a depression and a dome.

13. The osteosynthesis clip of claim 9, wherein the two elongated sections include respective bulges that together form a space of separation between elongated sections.

14. The osteosynthesis clip of claim 9, wherein the elongated sections include respective stepped-up sections to permit the setting of bone fragments having varying diameters.

15. The osteosynthesis clip of claim 9, wherein the two engagement legs are a predetermined distance apart from each other, the predetermined distance equal to a desired post surgery distance between a first and second bore, wherein the first bore is drilled in a first bone member for receiving the first engagement leg and the second bore being drilled in a second bone member for receiving the second engagement leg.

16. The osteosynthesis clip of claim 9, wherein the at least two engagement legs have at least one straight side.

17. The osteosynthesis clip of claim 9, wherein the at least two engagement legs have at least one rounded side, are circular in cross section or square in cross section.

18. The osteosynthesis clip of claim 9, wherein only one side of each of the at least two engagement legs have respective helical screw surfaces extending along substantially an entire distance between respective tip portions and respective opposite portions.

19. The osteosynthesis clip of claim 9, wherein substantially the entire perimeter of the engagement legs have helical screw surfaces extending along substantially the entire distance between respective tip portions and respective opposite portions.

20. The osteosynthesis clip of claim 19, wherein the at least two engagement legs are circular in cross section.

21. The osteosynthesis clip of claim 9, wherein the shape memory alloy is also a biocompatible material.

22. The osteosynthesis clip of claim 21, wherein the two elongated sections include respective bulges that together form a space of separation between elongated sections.

23. The osteosynthesis clip of claim 21, wherein the elongated sections include respective stepped-up sections to permit the setting of bone fragments having varying diameters.

24. An improved osteosynthesis clip for the cicatrization of bone tissue fragments, the clip comprising:
  at least two engagement legs extending approximately parallel to one another and including respective tip portions to be inserted into the bone tissue fragments;
  a connecting bridge coupled to portions of the at least two engagement legs opposite the tip portions, the connecting bridge including at least two elongated sections extending along side one another, the elongated sections extending along a non-linear trajectory to form a non-linear deformable region;
  the elongated sections of the connecting bridge having top surfaces for receiving percussion blows to allow the engagement legs to be hammered into the bone tissue fragments;
  wherein the engagement legs have respective helical screw surfaces extending along substantially an entire distance between respective tip portions and respective opposite portions to facilitate removal of the clip after the bone tissue fragments have fused and the connecting bridge is severed; and
  wherein the at least two engagement legs have tapering cross sectional areas that continuously decrease as they extend from the bridge toward the tip portions along substantially an entire distance between the bridge and the tip portions.

25. An improved osteosynthesis clip for the cicatrization of bone tissue fragments, the clip comprising:
  at least two engagement legs extending approximately parallel to one another and including respective tip portions to be inserted into the bone tissue fragments;
  a connecting bridge coupled to portions of the at least two engagement legs opposite the tip portions, the connecting bridge including at least two elongated sections extending along side one another, the elongated sections extending along a non-linear trajectory to form a non-linear deformable region;
  the elongated sections of the connecting bridge having top surfaces for receiving percussion blows to allow the engagement legs to be hammered into the bone tissue fragments;
  wherein the engagement legs having respective helical screw surfaces extending along substantially an entire distance between respective tip portions and respective opposite portions to facilitate removal of the clip after the bone tissue fragments have fused and the connecting bridge is severed; and
  wherein substantially the entire perimeter of the engagement legs have helical screw surfaces extending along substantially the entire distance between respective tip portions and respective opposite portions;
  wherein the at least two engagement legs have tapering cross sectional areas that continuously decrease as they extend from the bridge toward the tip portions along substantially an entire distance between the bridge and the tip portions.

26. The osteosynthesis clip of claim 25, wherein the at least two engagement legs are circular in cross section.

* * * * *